United States Patent [19]

Frei et al.

[11] 4,144,877

[45] Mar. 20, 1979

[54] INSTRUMENT FOR VISCOELASTIC MEASUREMENT

[75] Inventors: Ephraim H. Frei; Bruce D. Sollish; Shmuel Yerushalmi, all of Rehovot, Israel

[73] Assignee: Yeda Research and Development Co. Ltd., Rehovoth, Israel

[21] Appl. No.: 713,891

[22] Filed: Aug. 12, 1976

[51] Int. Cl.² ............................................... A61B 5/10
[52] U.S. Cl. ..................................... 128/2 S; 128/2 R; 128/2.05 E; 307/88 ET
[58] Field of Search ................ 128/2 R, 2 S, 2.05 E, 128/2.05 D, 2.05 A, 2.05 P, 2.06 E, 2.1 R, 2.1 A, 2.1 Z; 307/88 ET

[56] References Cited

U.S. PATENT DOCUMENTS

| Re. 20,680 | 3/1938 | Sawyer | 128/2.1 R |
|---|---|---|---|
| 2,755,796 | 7/1956 | Boucke | 128/2 R |
| 3,239,696 | 3/1966 | Burkhalter et al. | 128/2.05E |
| 3,417,743 | 12/1968 | Carrera | 128/2 S |
| 3,607,754 | 9/1971 | Asahina et al. | 307/88 ET |
| 3,831,588 | 8/1974 | Rindner | 128/2 H |
| 3,845,771 | 11/1974 | Vise | 128/404 |
| 3,880,145 | 4/1975 | Blick | 128/2.05 A |
| 3,894,243 | 7/1975 | Edelman et al. | 179/111 ET |
| 3,970,862 | 7/1976 | Edelman et al. | 29/592 X |
| 3,996,922 | 12/1976 | Basham | 128/DIG. 29 |

OTHER PUBLICATIONS

DeGowin & DeGowin, "Bedside Diagnostic Exam.", MacMillan Co., Chic. 1969 pp. 274-277-329-333.
Freedman, A. M. et al., Modern Synopsis of Psychiatry, Chapter 22, Williams & Wilkins, Balt. Md., 1972 pp. 410-411.
Bailey'Histology, by Copenhauer, Bonge & Bonge, 1971, Williams & Wilkins Co., Balt., p. 285.
Guyton's Medical Physiology, 1971, W. B. Saunders Co., Phila., pp. 565-566.
Human Nervous System, Barr, 1972, Harper & Row, Hagerstown, Md., pp. 31-33.

*Primary Examiner*—Robert W. Michell
*Assistant Examiner*—Francis J. Jaworski
*Attorney, Agent, or Firm*—Ostrolenk, Faber, Gerb & Soffen

[57] ABSTRACT

An instrument for viscoelastic measurement, particularly for breast palpation, uses a sensing transducer head which contains at least two spaced, relatively small area transducers. The transducers can be fixed relative to a glove to be worn by an examiner or can be otherwise supported. The transducers have output leads connected to monitoring circuits which monitor differences in output of the transducers when both are pressed against breast tissue in order to sense thickened areas which may be too small to be sensed by manual palpation. The transducer may be attached to a position monitor so that the transducer head output can be continuously related to the location in space of the transducer head, and the output can be displayed in a suitable display.

14 Claims, 8 Drawing Figures

INSTRUMENT FOR VISOELASTIC MEASUREMENT

BACKGROUND OF THE INVENTION

This invention relates to apparatus and method for viscoelastic measurement to discover thickened regions in human tissue, and more specifically relates to a novel transducer head with at least two spaced transducer elements of small area to enable improved examination of human tissue, particularly breast tissue, whereby very small thickened regions can be discovered, and whereby the palpation procedure can be done more quickly than at present, and can be carried out with relatively little training of the examiner.

Three main methods are at present used for the diagnosis of breast cancer: X-ray—mammography, thermography and palpation. Some work is also being done with ultrasonic waves. None of these methods is adequate alone, nor is a combination of several of them satisfactory. Palpation, in general, is not able to detect tumors of less than about one centimeter is size.

One of the most accurate methods in use is plapation, but this is done manually, is subjective, is time-consuming, and is costly. No instrument has so far been developed to carry out the palpation method. This is mainly due to the fact that no well working transducer can transform the information related to the tactile sense into electronic signals in the range of the consistencies (mechanical impedance) of living tissue.

The present invention provides a novel instrument to obtain the same information as a physician obtains through palpation, which instrument can analyze viscoelastic properties better, which can permit the recording of the information and which provides an objective, rapid, and reliable method to diagnose pathological states especially breast cancer.

BRIEF DESCRIPTION OF THE INVENTION

In accordance with the invention, a plurality of small piezoelectric elements, which are spaced from one another, are arranged in a suitable array. The transducer elements may be in the form of spaced fingers one to five millimeters wide and spaced by one to five millimeters. The fingers can be laterally spaced from one another, or a plurality of fingers can surround a central finger, or any other array can be used. The transducer elements are then suitably secured relative to one another, for example at the fingertip of the flexible glove. Thus, the user's finger can press the transducer elements into a local tissue area, applying about the same pressure to each transducer element, and each transducer element will develop an output related to the consistency of the tissue beneath the individual transducer element. A difference in the output of one transducer element from that of an adjacent transducer element can then identify either the border or body of a thickened tissue region of very small diameter, much smaller than the least diameter lump which a skilled physician might detect when manually palpating a patient.

This information regarding the consistency of the tissue beneath each transducer element may be presented on an X—Y recorder to record the position of the transducer at each position, and also record the value of the stress encountered at that position. This could be done with present commercially available X—Y recorders, by vibrating the pen of this recorder, so-called "Z" presentation. A storage oscilloscope could also be used. As the stress in normal cases will change appreciably from location to location when scanning the breast, it may be desirable to record nonlinearity of the stress-strain dependence to show better significant changes in consistency of the underlying tissue.

In order to speed up the procedure, several transducer heads can be simultaneously operated. Thus, there may be several pens recording in parallel on the X—Y recorder, or several traces recording in parallel on the storage oscilloscope. It is also possible to record the difference of the signal of two adjacent transducers.

Any desired transducer material can be used for the elements, such as piezoelectric ceramic transducers, differential transformers, pliable resistors which change resistance with pressure and piezoelectric electret transducers. Electrets are made of organic compounds typically formed by cooling from liquid or soft state to the solid state in the presence of an electric field or by polymerization in the presence of an electric field. Conducting electrodes are deposited by known means. Typical materials used to make electrets are beeswax and polymers such as polyvenylidene fluoride. The electrodes can be in individual or array configuration. Such electrets are useful as the transducer elements since their mechanical impedance is well matched to the impedance of living tissue. Moreover, the consistency of an electret can be widely changed by using different substances of different combinations of substances. The matching of the impedance of the transducer to the tissue being examined has the advantage of higher sensitivity, better signal-to-noise ratio, and more comfort during the test.

As described before, the transducer itself exerts a strain on tissue and the stress, resulting from this strain is being measured. But palpation with such a transducer can also be done by inducing a variable strain with another (active) element on a nearby location of the tissue. The strain and stress resulting with be transmitted through the tissue and will give a signal at the transducer. To give a very simple example, a small hard part of the tissue is moved by the straining element below the transducer. In such a case, the transducer will indicate a higher stress when the hard tissue passes below it.

If desired, the signal produced by the transducer head can be processed through a computer which also can control the positions of the transducer or transducers. This computer could go into different modes, for instance to scan in detail any suspect area.

The instrument of the invention can be advantageously used for:

(a) Screening a large number of patients with the help of a technician only and print a record of the procedure.

(b) The novel transducer can measure fine differences of consistency to get a better differentiation of different pathologies.

(c) A transducer element can be smaller than a human finger. Thus, it can detect tumors of a smaller size than is possible at present with palpation.

DETAILED DESCRIPTION OF THE DRAWINGS

Figure 1:
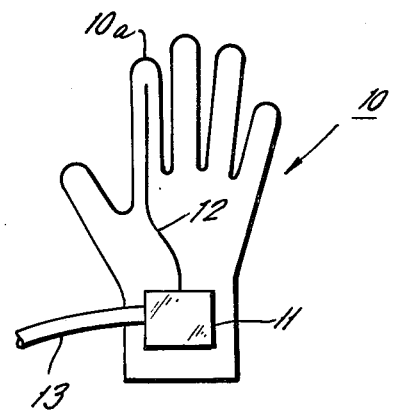
FIG. 1 is a top plan view of a glove which is equipped with the transducer head of the present invention and which contains a lead connector on the back of the glove which is provided with an output conductor which leads to appropriate processing circuits.

Referring first to FIG. 1, there is illustrated a plan view of the back of a flexible glove 10 which has an electrical connector 11 secured to the back thereof. The electrical connector receives an input cable 12 coming from a transducer head (not visible in FIG. 1) which lies along the front side extending from the tip of the forefinger. Connector 11 also has an output conduit 13 leading from glove 10 to appropriate processing circuits. The construction of glove 10 may be of the form of the conventional surgeon's glove and at least the glove portion receiving the transducer head will be extremely thin so as to not interfere with the application of uniform pressure between the transducer head and the tissue which is to be palpated.

Figure 2:
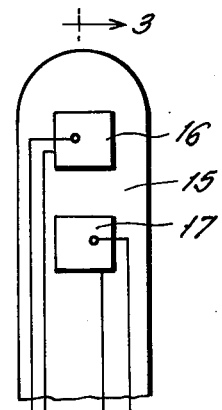
FIG. 2 is an enlarged view of a transducer head insert which is to be fixed inside the front tip of the forefinger of the glove of FIG. 1 with the transducer elements facing outwardly of the glove.
Figure 3:
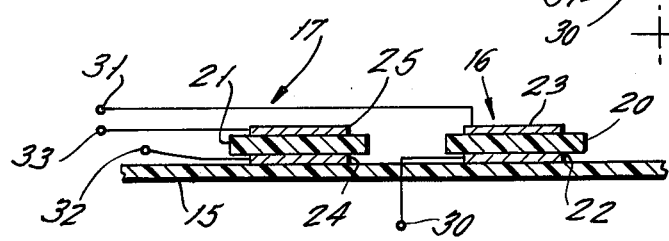
FIG. 3 is a cross-sectional view of FIG. 2 taken across the section line 3—3 in FIG. 2.

FIG. 2 and 3 illustrate one example of a transducer head construction which can be fitted into the forefinger of the glove of FIG. 1. In FIGS. 2 and 3, the transducer head insert consists of a thin, flexible rubber membrane support 15 which has cemented thereto a pair of spaced transducer elements 16 and 17. While the transducers 16 and 17 may be of any desired type, they are preferably formed of a type which is matched to the impedance of human tissue.

One commercially available piezoelectric transducer material which has been used in connection with the present invention, known by the trademark "Dynacon", is a rubber material impregnated with a conductive material and which exhibits good piezoelectric properties at relatively low pressure. Electrets are also useful as the transducer elements of the invention since they have an impedance which is fairly well matched to the impedance of human tissue.

The transducer elements 16 and 17 consist of a central transducer layer of the electret or rubber or other material 20 and 21, respectively, and electrodes are painted or deposited on the opposite surfaces of the piezoelectric bodies shown as electrodes 22 and 23 on body 20 and electrodes 24 and 25 on body 21. Electrodes 22, 23, 24 and 25 are then connected to suitable leads which are schematically connected in FIGS. 2 and 3 as the leads terminating with terminals 30, 31, 32 and 33. While lead 30 is schematically illustrated for clarity in FIG. 3 as penetrating the support membrane 15, in fact all leads may be cemented to the top of the membrane 15.

Figure 4:
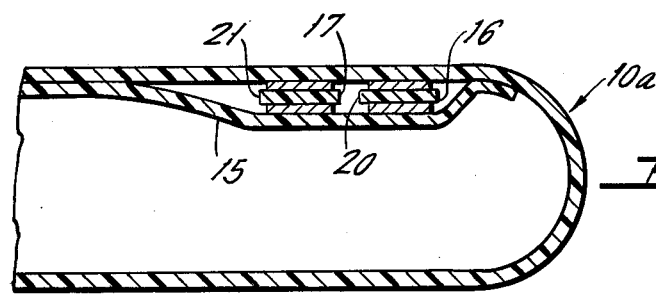
FIG. 4 is an enlarged cross-sectional view of the forefinger of the glove of FIG. 1 illustrating the transducer head assembly of FIGS. 2 and 3 affixed therein.

Each of the two transducer elements 16 and 17 of FIGS. 2, 3 and 4 are relatively small in area and typically may be about five millimeters by five millimeters in area and about one millimeter in thickness. The elements may have areas of from one to five millimeters to from one to five millimeters, or less, and can have thicknesses less than one millimeter. The transducer elements can have any desired surface shape other than the square shape illustrated.

The entire assembly of FIGS. 2 and 3 may then be cemented into the front fingertip 10a of the glove 10 of FIG. 1, as shown in FIG. 4. Thus, the upper surface of the transducers is covered by the thin membrane of glove fingertip 10a which, however, is made sufficiently thin so as to not interfere with the transfer of energy from the transducer elements 16 and 17 to the tissue being palpated beneath the fingertip 10a.

The transducer members 16 and 17 are also spaced from one another by about five millimeters' spacing between their adjacent parallel edges. The spacing chosen can be less than five millimeters, and will be related to the geometry of the particular transducer element. The transducer elements 16 and 17 are so positioned within fingertip 10a that the user of the glove has the transducer elements located near the center of his fingertip so that the two transducer heads 16 and 17 can be pressed against tissue being palpated in a manner which closely resembles the manual palpation technique.

The closely spaced transducer elements 16 and 17, however, will produce different outputs if they are pressed against tissue region containing some small thickened area beneath or partly beneath one transducer but not the other. Thus, an extremely sensitive output is produced from the transducer head arrangement which could not be produced by manual palpation since the palpation method can seldom sense thickened regions less than about one centimeter in diameter.

Figure 5:
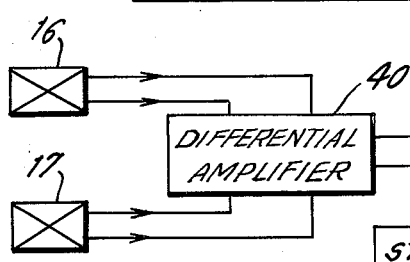
FIG. 5 is a block diagram illustrating one processing circuit arrangement which could be used in connection with the transducer arrangement of FIGS. 2, 3 and 4.

FIG. 5 illustrates one circuit diameter for processing the output signals of the piezoelectric transducers 16 and 17. Thus, in use, the transducers 16 and 17 of FIG. 5 are each pressed against human tissue, such as breast tissue, and output signals are produced from the transducers 16 and 17 which are related to the viscoelastic properties of the tissue being strained. These output signals are then applied to a differential amplifier 40 which will measure a difference between the two output signals which would be indicative of a difference in the viscoelastic properties of the tissue beneath transducers 16 and 17. The differential amplifier output may then be connected to a suitable display 41. At the same time, the output signals from differential amplifier 40 may be connected to a suitable storage medium 42, whereby the output signals can be stored and later processed in any desired manner as by computer processing for display in a recorder, which display would be coordinated with the X—Y coordinates of the transducer head arrangement. For this purpose, the transducer head arrangement of FIG. 2 can be connected to an X—Y coordinate generator of any well-known variety.

In the example of FIGS. 2, 3 and 4, the transducer head construction used only two transducer elements 16 and 17 which were spaced from one another. It should be understood that the present invention contemplates the use of any number of transducer elements arranged relative to one another in any pattern and the use of the two spaced transducer elements simply illustrate the basic concept of the invention. It should further be noted that the transducer elements may be dimensioned smaller than the illustrative five millimeters by five millimeters and may have closer spacings than disclosed in order to increase the sensitivity of the device.

It is not necessary to arrange the transducer head in the finger of a glove and, if desired, a transducer matrix can be arranged on a flexible membrane which could, for example, contain an array of one hundred transducer elements in a ten centimeter by ten centimeter area, with the elements being arranged in orthogonal rows and lines. This array may then be used for breast palpation by placing the array against the breast and then having the patient lie flat against a plate which will apply a pressure over the entire array, with the individual transducer of the array producing electric outputs related to the tissue viscoelastic properties immediately beneath the individual transducer element. The output signal of each transducer element may then be read out in a multiplex fashion to produce a suitable display and processed to determine differences between the outputs from adjacent issue regions.

An array such as the one described above is illustrated in FIGS. 6 and 7, wherein the array is mounted on a thin, flexible rubber membrane 15 which can have a thickness, for example, of one millimeter and wherein the array consists of ten rows of ten transducers arranged in ten columns orthogonal to the rows.

Figure 7:
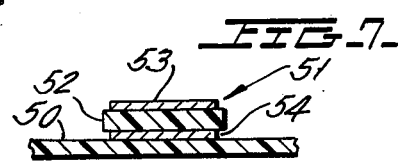
FIG. 7 is a cross-sectional view of FIG. 6 taken across the section line 7—7 in FIG. 6.

A typical transducer 51 of the array is shown in FIG. 7 as consisting of a transducer body 52 which consists of a rubber material impregnated with conductive material of the type known by the trademark "Dynacon", with painted electrodes 53 and 54 formed on the opposite surfaces of the transducer body 52. The transducer body 52 is then cemented to the flexible sheet 50.

Leads attached to the electrods 53 and 54 then extend from the electrodes of each of the transducers and into a suitable cable (not shown). Some of these leads are schematically shown in the upper left-hand corner of FIG. 6.

Figure 6:
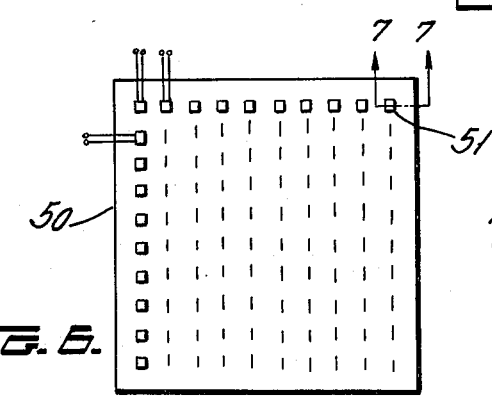
FIG. 6 is a plan view of the embodiment of the invention in which the large number of transducer arrangements are arranged in an array.

In the embodiments of FIGS. 6 and 7, the sheet 50 may be a sheet having a dimension of about ten centimeters by ten centimeters, with the individual transducer elements having a dimension of about five millimeters by five millimeters, the transducer being spaced fron one another by about five millimeters.

Figure 8:
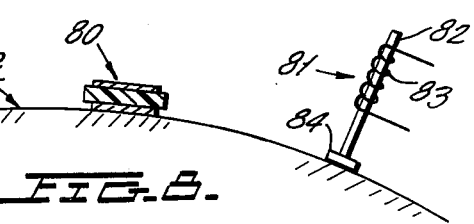
FIG. 8 is a side view illustrating the arrangement of the special element exerting stress.

FIG. 8 shows a further embodiment of the invention wherein a passive transducer 80, having the structure of FIG. 7, is spaced from five millimeters to several centimeters from head 81 applying a shear stress, which causes a shear strain in the tissue. Shear applying head 81 consists of a magnetic armature 82 surrounded by a solenoid 83 which is connected to a suitable electrical energizing source (not shown). A small rubber application pad 84 is connected to the bottom of armature 82. In addition, pulses to solenoid 83 cause stress to be applied to the tissue beneath applicator 84, with attendent stresses applied to passive transducer 80, depending upon the viscoelastic properties of the tissue between pad 84 and transducer 80.

Although a preferred embodiment of this invention has been described, many variations and modifications will now be apparent to those skilled in the art, and it is therefore preferred that the instant invention be limited not by the specific disclosure, herein but only by the appended claims.

The embodiments of the invention in which an exclusive privilege or property is claimed are defined as follows:

1. A transducer head for palpation of living breast tissue comprising, in combination: at least first and second pressure transducer means spaced from one another and mounted on a common base having a independently for engaging a plurality of fingers; said transducer means having sufficient sensitivity to detect viscoelastic changes in breast tissue; said first and second transducer means being generally flat and thin, and being normally disposed in a generally common plane; each of said transducer means having electrical output leads insulated from one another; and circuit means including differential output measuring means connected to each of said transducer means for determining a difference in output between said first and second transducer means when said first and second transducer means are pressed against spaced areas of living breast tissue, thereby to determine local thickened regions in said living breast tissue.

2. The transducer head of claim 1 wherein each of said transducers are less than about twenty-five square millimeters in area which can be pressed against living tissue, and wherein said transducers are spaced apart by less than about five millimeters.

3. The transducer head of claim 2 wherein said transducers have an acoustical impedance similar to the acoustical impedance of living tissue.

4. The transducer head of claim 2 wherein said common base comprises a thin, flexible membrane.

5. The transducer head of claim 1 wherein said transducer head is mounted within a glove, and is adjacent the fingertip of said glove.

6. The transducer head of claim 5 wherein said common base comprises a thin, flexible membrane.

7. The transducer head of claim 1 wherein said common base comprises a thin, flexible membrane.

8. The transducer head of claim 1 wherein said transducers are electrets.

9. The transducer head of claim 1 wherein said transducers have an acoustical impedance similar to the acoustical impedance of living tissue.

10. The transducer head of claim 4 wherein said transducers are piezoelectric elements comprised of bodies of polyvenylidene fluoride polymer.

11. The method of palpating a breast to determine the presence of thickened regions; said method comprising the manual application of a self-contained assemblage of a plurality of electromechanical pressure transducers to the surface of the breast tissue, the simultaneous pressing of each of said spaced electromechanical pressure transducers into respective underlying surface areas of the breast tissue, and measuring the output of the spaced transducers to determine output differences which are caused by differences in the viscoelastic properties of the tissue beneath the respective spaced transducers.

12. The method of claim 11 wherein each of said spaced pressure transducers are pressed into said surface areas for about the same distance.

13. The method of claim 11 wherein each of said spaced transducers are manually pressed into said surface areas by an examiner using a manual breast palpation technique.

14. A transducer head for palpation of living breast tissue comprising, in combination: at least first and second pressure transducers spaced from one another and mounted on a glove; said first and second transducers being generally flat and thin, and being normally disposed in a generally common plane; each of said transducers having electrical output leads; and first circuit means connected to said first transducer for causing said first transducer to apply a strain to the tissue beneath it, and output circuit means connected to said second transducer for developing an output signal from said second transducer in response to the strain on tissue between said first and second transducers.

* * * * *

UNITED STATES PATENT AND TRADEMARK OFFICE
CERTIFICATE OF CORRECTION

PATENT NO. : 4 144 877
DATED : March 20, 1979
INVENTOR(S) : Ephraim H. Frei et al It is certified that error appears in the above-identified patent and that said Letters Patent are hereby corrected as shown below:

At column 2, line 39, "with" should be -- will --

At column 5, line 17, "issue" should be -- tissue --

In claim 1, line 4, "a independently" should be -- a means -- line 5, "engaging" should be -- independently engaging --

Signed and Sealed this

Thirteenth Day of May 1980

[SEAL]

Attest:

SIDNEY A. DIAMOND

Attesting Officer     Commissioner of Patents and Trademarks